United States Patent [19]

Lang, Jr. et al.

[11] 4,118,498

[45] Oct. 3, 1978

[54] 2,6-BIS(1-PIPERIDINOALK-YLIDENEAMINO)ANTHRAQUINONES AND METHOD OF TREATING CECAL AND HEPATIC AMEBIC INFECTIONS THEREWITH

[75] Inventors: Stanley Albert Lang, Jr., Stoney Point; Paul Frank Fabio, Pearl River; Yang-I Lin, Nanuet; Keith Chadwick Murdock, Pearl River, N.Y.; Thomas Lynn Fields, Pearl River, all of N.Y.

[73] Assignee: American Cyanamid Company, Stamford, Conn.

[21] Appl. No.: 851,662

[22] Filed: Nov. 15, 1977

Related U.S. Application Data

[60] Continuation of Ser. No. 772,038, Feb. 25, 1977, abandoned, which is a continuation-in-part of Ser. No. 699,816, Jun. 24, 1976, abandoned, which is a division of Ser. No. 606,805, Aug. 22, 1975, abandoned.

[51] Int. Cl.$^2$ .................. C07D 21/10; A61K 31/445; C07D 295/12
[52] U.S. Cl. ................................. 424/267; 260/272; 260/293.62; 260/378; 542/415
[58] Field of Search ............... 542/415; 260/293.62, 260/272; 424/267; 8/39 R

[56] References Cited

U.S. PATENT DOCUMENTS

| | | | |
|---|---|---|---|
| 3,184,482 | 5/1965 | Steiger | 260/296 R |
| 3,974,186 | 8/1976 | Fleming et al. | 260/380 |

FOREIGN PATENT DOCUMENTS 2,521,357  11/1976  Fed. Rep. of Germany ........... 542/415

*Primary Examiner*—Natalie Trousof
*Assistant Examiner*—Richard A. Schwartz
*Attorney, Agent, or Firm*—Claude J. Caroli

[57] ABSTRACT

Novel 2,6-bis(1-piperidinoalkylideneamino)anthraquinones that are effective against cecal and hepatic amebic infestations in warm-blooded animals are disclosed.

10 Claims, No Drawings

2,6-BIS(1-PIPERIDINOALKYLIDENEAMINO)ANTHRAQUINONES AND METHOD OF TREATING CECAL AND HEPATIC AMEBIC INFECTIONS THEREWITH

CROSS REFERENCE TO RELATED APPLICATIONS

This application is a continuation of application Ser. No. 772,038, filed Feb. 25, 1977, now abandoned, which is a continuation-in-part of application Ser. No. 699,816, filed June 24, 1976, now abandoned, which is a division of application Ser. No. 606,805, filed Aug. 22, 1975, now abandoned.

DESCRIPTION OF THE PRIOR ART

U.S. Pat. No. 3,184,482 discloses a compound of the formula:

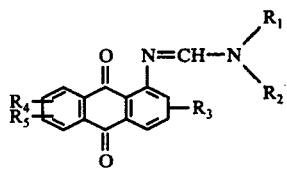

wherein $R_1$ and $R_2$ are hydrogen or lower alkyl and $R_3$, $R_4$, and $R_5$ are hydrogen, hydroxy or

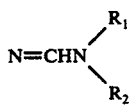

Utility is described as antibacterial, antiviral, antiprotozoal and anthelmintic.

U.S. Pat. No. 3,654,319, Neeff, make a gratuitous disclosure of a compound of the formula:

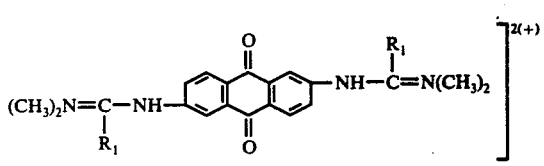

but the compound is neither claimed nor exemplified. Neeff does exemplify 1,4- and 1,5-diaminoanthraquinones of the following formulae:

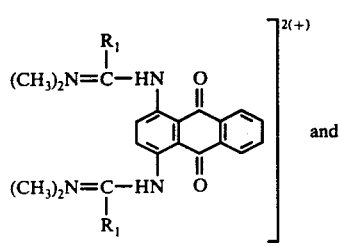

and

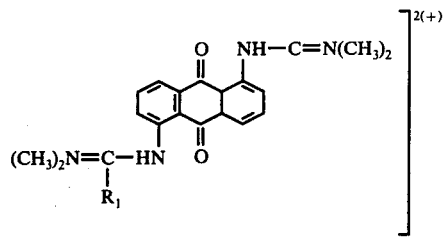

but Applicants have prepared these compounds and have found them to be inactive for the claimed utility.

BRIEF SUMMARY OF THE INVENTION

This invention is concerned with novel compounds of the formula:

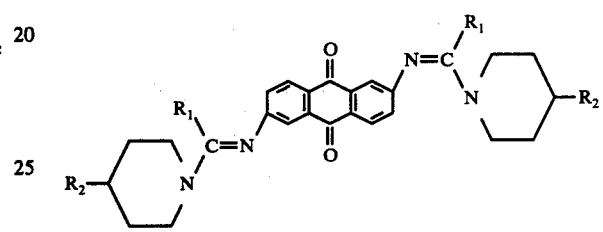

wherein $R_1$ is selected from the group consisting of hydrogen and lower alkyl ($C_1$-$C_4$) and $R_2$ is selected from the group consisting of hydrogen and lower alkyl ($C_1$-$C_2$) and pharmaceutically acceptable salts thereof. This invention is also concerned with the method of treating cecal and hepatic amebic infections in warm-blooded animals with the disclosed compounds.

DETAILED DESCRIPTION OF THE INVENTION

The compounds of the present invention are normally crystalline solids being soluble in dimethylformamide and dimethylsulfoxide and less soluble in chloroform, alcohol and acetone. The salts (mono and di) are readily soluble in water and less soluble in alcohol.

The compounds of the present invention may be prepared according to the following methods:

A. 2,6-Diaminoanthraquinone (1 mole) is reacted with a complex formed from phosphorous oxychloride (1.5 to 3 moles) and an N-acylpiperidine (2 to 6 or more moles) in a solvent such as acetonitrile (at a ratio of about 1-3 liters of solvent per mole of amine) at a temperature of 25° to 70° C. for a period of about one to 24 hours.

More specifically, to a solution of the N-acylpiperidine in the solvent is added phosphorous oxychloride at −5° to 20° C. The resulting mixture is stirred at 0° to room temperature for 30 minutes to 6 hours. The 2,6-diaminoanthraquinone is added and the reaction mixture is stirred at 25° to 70° C. for 1 to 24 hours. The reaction mixture is then poured into ice water and basified. The resulting crystals are collected by filtration and recyrstallized from an appropriate solvent or mixture of solvents such as chloroform/hexane.

B. 2,6-Diaminoanthraquinone (72 parts) is slurried in 300 parts of a triethyl ortho acid and 250 parts of acetic anhydride is added. The mixture is refluxed for 1 to 8 hours, cooled and the solid product is collected, washed and dried. Purification is accomplished by dissolving this crude product in 1000 parts of chloroform, filtration and concentration of the filtrate. Further purification may be realized by recrystallization from a solvent such as dimethylformamide. A bis-imino-ether (8 parts) is slurried in 45 parts of an appropriate amine. One equivalent of glacial acetic acid for each part of imino-ether is added and the slurry is heated in an oil bath at 100°–160° C. for 8 to 24 hours. (The use of a bomb is recommended with low boiling amines.) The reaction mixture is cooled. Products which crystallize are collected and recrystallized from a solvent such as methanol, ethanol, methyl cellosolve or dimethylformamide. For products which do not crystallize, the volatiles are removed in vacuo and the residue is dissolved in methanol. Upon cooling the product crystallizes and is recrystallized from a suitable solvent as above.

C. Diethyl N,N'-(2,6-anthraquinonylene) di-formimidate is combined with at least 2 molar equivalents of a piperidine and heated at a temperature of 130°–200° C. for 2 to 18 hours. The reaction mixture is stripped of volatiles under reduced pressure and the pure product is obtained by recrystallization from a suitable solvent.

The compounds of the present invention are active in treating cecal and hepatic amebic infections in warm-blooded animals. Two tests which establish this activity are as follows:

Organism

The organism used in both tests is the National Institute of Health 200μ strain of *Entamoeba histolytica*. This strain and an unidentified fecal flora are cultured in Cleveland-Collier Medium at 37° C. This medium consists of a liver infusion agar base overlaid with a horse serum:saline mixture (1:6) to which is added a few milligrams of sterile rice powder. The amebas are transferred to fresh medium twice weekly.

Cecal Infections in Female Albino Wistar Rats

Pooled overlay (0.25 ml) containing large numbers of amebas is injected into the cecums of anesthetized weanling rats during laparotomy. Treatment is begun on the day after inoculation. The compounds are dissolved or suspended in 0.2% aqueous agar and administered once daily, by gavage, for 5 consecutive days. Six days after inoculation of the amebas, the rats are sacrificed and a scraping from the cecal wall of each rat is mixed with a drop of 0.85% saline and examined microscopically for amebas. A rat is considered cured if no amebas are seen. The cure or clearance rate (number cured/number treated) for each regimen is calculated and corrected for non-specific cures observed in the untreated infected controls. An active dose is the lowest dose, in terms of mg/kg/day, which clears or cures 50% or more of the rats so treated. The results of typical compounds of the present invention appear in the following table together with results obtained using known effective drugs for comparison.

Hepatic Infections in Female Golden Hamsters

A piece of ameba-laden absorbable sponge, about 25 millimeters square, is inserted between the middle lobes of the livers of anesthetized hamsters during laparotomy. Untreated hamsters usually die from the resulting infection about 7 days after inoculation. Treatment is started on the day of inoculation as soon as the hamsters recover from the surgical anesthetic. The test compounds are dissolved or suspended in 0.2% aqueous agar and administered once daily, by gavage, for 5 consecutive days. Effective regimens prevent mortality. Survival rates are corrected for non-specific survival observed in untreated groups. An active dose is the lowest dose, expressed in mg/kg/day, which protects 50% or more of the hamsters so treated as evidenced by survival 14 days after inoculation. The results of typical compounds of the present invention appear in the following table together with the active dose of known effective drugs for comparison.

Table

| COMPOUNDS | CECAL INFECTION Lowest Active Dose mg/Kg/day | HEPATIC INFECTION Lowest Active Dose mg/Kg/day |
|---|---|---|
| 2,6-Bis(piperidinomethyleneamino)-anthraquinone | 20 | 100 |
| 2,6-Bis[(1-piperidinopropylidene)-amino]anthraquinone | 50 | — |
| 2,6-Bis[(1-piperidinoethylidine)-amino]anthraquinone | 50 | — |
| 2,6-Bis{[1-(4-methylpiperidino)-ethylidene]amino}anthraquinone | 10 | — |
| 6-n-Propyloxy-3-nitroimidazo[1,2-b]-pyridazine | 20 | 25 |
| 2-Methyl-5-nitroimidazole-1-ethanol | 10 | 10 |
| Nitrimidazine | 20 | 100 |
| Tinedazole | 5 | 25 |

The novel 2,6-bis(1-piperidinoalkylideneamino)anthraquinones of the present invention are useful for ameliorating cecal and hepatic amebic infections in warm-blooded animals when administered in amounts ranging from about 0.5 mg. per kg. to about 40 mg. per kg. of body weight per day. A preferred dosage regimen for optimum results would be from about 2 mg. per kg. to about 29 mg. per kg. Thus, the daily dosage employed for a subject of about 70 kg. of body weight is about 35 mg. to about 2.8 g., and preferably about 140 mg. to about 2.0 g.

Suitable oral preparations consist, for example, of capsules, tablets, troches, suspensions, syrups and the like. In the case of tablets the principal active ingredient is mixed with conventional ingredients such as corn starch, lactose, sucrose, sorbitol, talc, stearic acid, magnesium stearate, dicalcium phosphate, gums or similar materials as non-toxic pharmaceutically acceptable diluents or carriers.

Sustained release formulations are also contemplated by the present invention.

The liquid forms in which the novel compositions of the present invention may be incorporated for administration include suitably flavored emulsions with edible oils, such as, cottonseed oil, sesame oil, coconut oil, peanut oil and the like, as well as elixirs and similar pharmaceutical vehicles. Sterile suspensions or solutions can be prepared for parenteral use. Isotonic preparations containing suitable preservatives are also desirable for injectable use.

EXAMPLE 1

N,N'-(2,6-Anthraquinonylene)-di-formimidic acid diethyl ester

A 35.7 g portion of 2,6-diaminoanthraquinone is mixed with 100 ml of triethylorthoformate containing 5 drops of concentrated $H_2SO_4$. The mixture is heated to reflux and the alcohol is removed as it forms over a 2 hour period. The reaction mixture is cooled to $-10°$ C., the solid which forms is collected by filtration, washed with 2B alcohol and air dried. Recrystallization from dimethylformamide produces brown crystals, mp 235°–250° C.

EXAMPLE 2

2,6-Bis(piperidinomethyleneamino)anthraquinone

A mixture of 7.0 g of N,N'-(2,6-anthraquinonylene)-di-formimidic acid diethyl ester and 7.48 g of piperidine is heated in an oil bath at 130°–140° C. for 2 hours and then allowed to stand at room temperature overnight. The reaction mixture is triturated with two 50 ml portions of hexane and the brown solid is air dried. This solid is recrystallized from 275 ml of boiling methyl cellosolve which is filtered while hot and then cooled to 4° C. The solid is washed with methyl cellosolve and with 2B alcohol and dried at 78° C. in vacuo over $P_2O_5$ giving an orange solid, mp 229°–233° C.

EXAMPLE 3

N,N'-2,6-Anthraquinonylenedi-acetimidic acid diethyl ester

A mixture of 35.7 g of 2,6-diaminoanthraquinone, 100 ml of triethylorthoacetate and 6 drops of concentrated sulfuric acid is heated for 6 hours in an oil bath at 130° C. with a take-off condenser and four inch Vigreux Column. A 5 ml portion of ethyl alcohol is collected, then the mixture is allowed to stir at room temperature overnight. An additional 60 ml of triethylorthoacetate is added, the mixture is refluxed for 6 hours longer and is allowed to stir overnight at room temperature. The brownish solid collected by filtration is washed with ether and dried in vacuo. A 10 g portion of the above product is recrystallized from 400 ml of methyl cellosolve, the solid is filtered and washed twice with ether and is dried in vacuo at 50° C. to give orange-tan crystals.

A 1.0 g portion of the brownish solid previously described is recrystallized from 100 ml of dimethylformamide to give orange crystals after drying in vacuo at 50° C. The recrystallized materials are combined to give the final product, mp 195°–197° C.

EXAMPLE 4

2,6-Bis[(1-piperidinopropylidene)amino]anthraquinone

A mixture of 8.12 g of N,N'-2,6-anthraquinonylenedipropionimidic acid diethyl ester and 40 ml of piperidine is heated in an oil bath at 115° C. with a reflux condenser for 18 hours. The condenser is removed and the mixture is heated an additional hour, then is concentrated in vacuo to a brown syrup. The syrup is then stirred with 100 ml of diethyl ether resulting in a brown solid which is filtered and washed with ether, then dried in vacuo. The dried product is recrystallized from 40 ml of dimethylformamide to give dark yellow crystals, mp 183°–185° C.

EXAMPLE 5

2,6-Bis[(1-piperidinoethylidene)amino]anthraquinone

A mixture of 7.56 g of N,N'-2,6-anthraquinonylenediacetimidic acid diethyl ester and 40 ml of piperidine is heated in an oil bath at 120° C., with a reflux condenser for 20 hours. The condenser is removed and the mixture heated an additional hour, then is concentrated in vacuo to a dark syrup. The syrup is triturated with 100 ml of diethyl ether, the resulting orange solid is collected by filtration, washed with ether and is dried in vacuo. The dried material is recrystallized from 40 ml of dimethylformamide to give yellow crystals, mp 233°–235° C.

EXAMPLE 6

2,6-Bis{{[4-(3-dimethylaminopropyl)piperidino]methylene}amino}anthraquinone

A suspension of 7.0 g of N,N'-(2,6-anthraquinonylene)-di-formimidic acid diethyl ester and 15.0 g of 4-(3-dimethylaminopropyl)-piperidine is heated in an oil bath at 160° C. for 3 hours in a flask fitted with a short Vigreux Column fused to a take-off condenser during this time the 78° C. distillate is allowed to boil off. The reaction mixture is allowed to cool in the oil bath then is slurried with hexane and filtered. The solid is dissolved in 100 ml of boiling dimethylformamide and is filtered hot. The resulting filtrate is cooled at $-10°$ C. and filtered to obtain an orange solid. This solid is recrystallized from 25 ml of methyl cellosolve and is filtered hot to clarify. The filtrate is cooled at $-10°$ C. and the orange solid is collected. The product is then dried in vacuo at 78° C. over phosphorous pentoxide to give an orange solid, mp 171°–174° C.

EXAMPLE 7

2,6-Bis{[1-(4-methylpiperidino)ethylidene]amino}anthraquinone

A 7.56 g portion of N,N'-2,6-anthraquinonylenediacetimidic acid diethyl ester and 40 ml of 4-methylpiperidine are heated in an oil bath at 130° C. with a reflux condenser for 18 hours. The mixture is cooled in an ice bath, the orange solid is collected by filtration, washed with ether and dried in vacuo at 80° C. This solid is recrystallized from 100 ml of methyl cellosolve and the yellow crystals are dried in vacuo at 80° C., mp 200°–202° C.

EXAMPLE 8

2,6-Bis{[1-(4-methylpiperidine)propylidene]amino}anthraquinone

A mixture of 8.12 g of N,N'-2,6-anthraquinonylenedipropionimidic acid diethyl ester and 40 ml of 4-methylpiperidine is heated with a reflux condenser at 130° C. for 18 hours. The reaction mixture is cooled in an ice bath and is filtered.

The filtrate is concentrated in vacuo to a dark brown gum which is taken up in 50 ml of methyl cellosolve with heating. The solution is stored in a freezer for 2 hours. The product is collected by filtration and is washed with a small amount of methyl cellosolve then with diethyl ether. The product is dried in vacuo at 80° C. to give yellow crystals, mp 150°–153° C.

EXAMPLE 9

2,6-Bis{[(4-methylpiperidino)methylene]amino}anthraquinone

A mixture of 6.8 g of N,N'-(2,6-anthraquinonylene)-di-formimidic acid diethyl ester and 8.93 g of 4-methylpiperidine is heated in an oil bath at 140° C. for 2 hours in a flask fitted with a short Vigreux Column fused to a take-off condenser, during this time the 78° C. distillate is allowed to boil off. The reaction mixture is allowed to cool in the oil bath overnight, then is triturated with two 50 ml portions of hexane. The rust brown solid is air dried, recrystallized from 275 ml of boiling methyl cellosolve and filtered hot to clarify. The filtrate is cooled to 4° C. and the solid is filtered and washed with methyl cellosolve followed by 2B ethyl alcohol. The product is dried in vacuo at 78° C. over phosphorous pentoxide to give an orange solid, mp 229°–233° C.

EXAMPLE 10

2,6-Bis(piperidinomethyleneamino)anthraquinone dihydrochloride trihydrate

A 6.1 g portion of 2,6-bis(piperidinomethyleneamino)anthraquinone, as prepared in Example 12, is slurried in 300 ml of chloroform and is filtered. To the filtrate is added 10 ml of 4.5N hydrochloric acid in isopropyl alcohol resulting in formation of a pale orange precipitate which is stored at −10° C. then is filtered. The collected product is washed on the filter with chloroform and is dried at 78° C. in vacuo over phosphorous pentoxide to give a pale orange solid as the trihydrate of the dihydrochloride.

EXAMPLE 11

2,6-Bis(α-piperidinobenzylideneamino)anthraquinone

To a stirred solution of 28.6 g of benzoylpiperidine in 150 ml of acetonitrile maintained at 5°–10° C. in an ice-water bath is added 18.4 g of phosphorous oxychloride. The ice-water bath is removed and the resulting mixture is stirred at room temperature for 1 hour. A 11.9 g portion of 2,6-diaminoanthraquinone is then added and the mixture is stirred at 60° C. for 10 hours. The reaction mixture is then poured into 500 ml of ice-water and made basic with 5N sodium hydroxide solution. The product is formed as orange crystals which are collected by filtration and are washed with water. The product is then recrystallized from chloroform/acetone to give orange crystals, mp 264°–266° C.

EXAMPLE 12

N',N'''-(2,6-Anthraquinonylene)bis-N-piperidino-N-p-chlorobenzylidene

To a stirred solution of 33.55 g of p-chlorobenzoyl piperidine in 100 ml of acetonitrile cooled at 5°–15° C. in an ice-water bath is added 10.8 ml of phosphorous oxychloride over a 30 minute period. The ice-water is removed and stirring is continued at room temperature for 30 minutes, then 11.9 g of 2,6-diaminoanthraquinone is added and stirring is continued at room temperature for 1 hour, then at 60° C. for 20 hours. The reaction mixture is then cautiously poured into a mixture of 500 ml of ice-water and stirring is continued for one hour gradually adding 75 ml of 10N sodium hydroxide. The reddish solid is collected by filtration, is washed with water and is dried in vacuo at 80° C. The dried material is slurried in 300 ml of chloroform and is filtered. The filtrate is washed 4 times with water, is dried over magnesium sulfate, is filtered and concentrated in vacuo. The residue is slurried with 50 ml of methyl alcohol and is filtered to collect the orange crystals which are washed with diethyl ether. The product is dried in vacuo to give orange crystals, mp 275°–277° C.

We claim:

1. A compound of the formula:

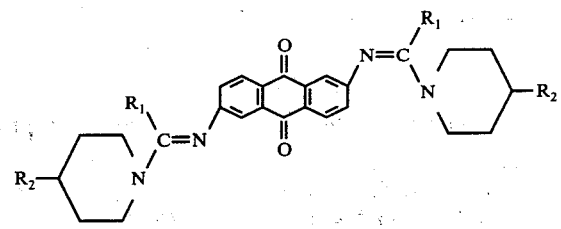

wherein $R_1$ is selected from the group consistng of hydrogen and lower alkyl ($C_1$–$C_2$) and $R_2$ is selected from the group consisting of hydrogen and lower alkyl ($C_1$–$C_2$) and pharmaceutically acceptable salts thereof.

2. The compound according to claim 1, 2,6-bis(piperidinomethyleneamino)anthraquinone.

3. The compound according to claim 1, 2,6-bis[(1-piperidinopropylidene)amino]anthraquinone.

4. The compound according to claim 1, 2,6-bis[(1-piperidinoethylidene)amino]anthraquinone.

5. The compound according to claim 1, 2,6-bis[1-(4-methyl-piperidinoethylidene)amino]anthraquinone.

6. A method of treating cecal and hepatic amebic infections in warm-blooded animals which comprises administering to said animals an amount effective against said infections of a compound of the formula:

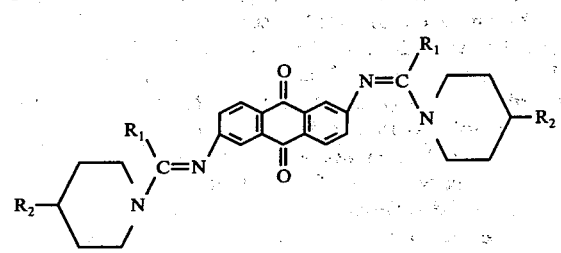

wherein $R_1$ is selected from the group consisting of hydrogen and lower alkyl ($C_1$–$C_2$) and $R_2$ is selected from the group consisting of hydrogen and lower alkyl ($C_1$–$C_2$) and pharmaceutically acceptable salts thereof.

7. The method according to claim 6 wherein the compound is 2,6-bis(piperidinomethyleneamino)anthraquinone.

8. The method according to claim 6 wherein the compound is 2,6-bis(1-piperidinopropylidene)amino anthraquinone.

9. The method according to claim 6 wherein the compound is 2,6-bis[(1-piperidinoethylidene)amino]anthraquinone.

10. The method according to claim 6, wherein the compound is 2,6-bis[1-(4-methyl-piperidinoethylidene)amino]anthraquinone.

* * * * *